(12) United States Patent
Huynh et al.

(10) Patent No.: US 11,577,247 B2
(45) Date of Patent: Feb. 14, 2023

(54) DETERMINING A BULK CONCENTRATION OF A TARGET IN A SAMPLE USING A DIGITAL ASSAY WITH COMPARTMENTS HAVING NONUNIFORM VOLUMES

(71) Applicant: Tokitae LLC, Bellevue, WA (US)

(72) Inventors: Toan Huynh, Seattle, WA (US); Bernhard Hans Weigl, Seattle, WA (US); Samantha A. Byrnes, Seattle, WA (US); Kevin Paul Flood Nichols, Issaquah, WA (US)

(73) Assignee: Tokitae LLC, Bellevue, WA (US)

( * ) Notice: Subject to any disclaimer, the term of this patent is extended or adjusted under 35 U.S.C. 154(b) by 0 days.

(21) Appl. No.: 17/689,539

(22) Filed: Mar. 8, 2022

(65) Prior Publication Data

US 2022/0193661 A1 Jun. 23, 2022

Related U.S. Application Data

(63) Continuation of application No. 16/200,447, filed on Nov. 26, 2018, now Pat. No. 11,305,284.

(51) Int. Cl.
*B01L 3/00* (2006.01)
*C12Q 1/6816* (2018.01)
*G01N 33/18* (2006.01)

(52) U.S. Cl.
CPC .......... *B01L 3/5082* (2013.01); *C12Q 1/6816* (2013.01); *B01L 2200/18* (2013.01);
(Continued)

(58) Field of Classification Search
CPC ........... B01L 3/5082; B01L 2400/0433; B01L 2300/0663; B01L 2200/18;
(Continued)

(56) References Cited

U.S. PATENT DOCUMENTS

2013/0302792 A1   11/2013   Hindson et al.
2017/0175174 A1*  6/2017    Chiu ................... G06V 20/695

FOREIGN PATENT DOCUMENTS

EP         3299470 A1   3/2018
JP      2015504305 A    2/2015
(Continued)

OTHER PUBLICATIONS

Extended European Search Report and Search Opinion for European Patent Application No. 19890189.4 dated Jul. 4, 2022, 7 pages.
(Continued)

*Primary Examiner* — Jennifer Wecker
*Assistant Examiner* — Oyeleye Alexander Alabi
(74) *Attorney, Agent, or Firm* — AEON Law, PLLC; Adam L. K. Philipp; Shan Liao

(57) ABSTRACT

An embodiment of a system includes a compartment-generating device, a compartment detector, and electronic computing circuitry. The device is configured to generate compartments of a digital assay, at least one of the compartments having a respective volume that is different from a respective volume of each of at least another one of the compartments. The detector is configured to determine a number of the compartments each having a respective number of a target that is greater than a threshold number of the target. And the electronic circuitry is configured to determine a bulk concentration of the target in a source of the sample in response to the determined number of compartments. Because such a system can be configured to estimate a bulk concentration of a target in a source from a polydisperse digital assay, the system can be portable, and lower-cost and faster, than conventional systems.

15 Claims, 11 Drawing Sheets

(52) U.S. Cl.
CPC ............... *B01L 2300/0663* (2013.01); *B01L 2300/0832* (2013.01); *B01L 2400/0433* (2013.01); *G01N 33/18* (2013.01)

(58) Field of Classification Search
CPC ..... B01L 2300/0832; B01L 2200/0673; C12Q 1/6816; C12Q 1/6844; G01N 33/18
See application file for complete search history.

(56) References Cited

FOREIGN PATENT DOCUMENTS

| | | | |
|---|---|---|---|
| JP | 2017062250 | A | 3/2017 |
| JP | 2017519484 | A | 7/2017 |
| JP | 2018046819 | A | 3/2018 |
| WO | 2012100198 | A2 | 7/2012 |
| WO | 2013072069 | A1 | 5/2013 |
| WO | 2015157369 | A1 | 10/2015 |
| WO | 2019089996 | A1 | 5/2019 |

OTHER PUBLICATIONS

Office Action received for Japanese Patent Application No. 2021-529411, dated Nov. 8, 2022, 7 pages (3 pages of Official Language and 4 pages of English Translation).

\* cited by examiner

DETERMINING A BULK CONCENTRATION OF A TARGET IN A SAMPLE USING A DIGITAL ASSAY WITH COMPARTMENTS HAVING NONUNIFORM VOLUMES

CROSS-REFERENCE TO RELATED APPLICATIONS

This application is a continuation of non-provisional U.S. patent application Ser. No. 16/200,447, filed Nov. 26, 2018, titled DETERMINING A BULK CONCENTRATION OF A TARGET IN A SAMPLE USING A DIGITAL ASSAY WITH COMPARTMENTS HAVING NONUNIFORM VOLUMES, and naming first inventor HUYNH, Toan.

The entire contents of the above-referenced applications and of all priority documents referenced in the Application Data Sheet filed herewith are hereby incorporated by reference for all purposes.

SUMMARY

Although examples of one or more embodiments, and examples of problems solved by one or more embodiments, are described with reference to sample droplets of disparate volumes suspended in a liquid, one or more embodiments relate generally to techniques for determining a bulk concentration of a target in a source from a digital assay including compartments of disparate volumes formed in a barrier phase.

There are situations in which it is desirable to determine a bulk concentration of a target in a source. For example, to ensure the safety of a large number of people, a government agency may want to determine a bulk concentration of a pathogen (e.g., anthrax or another infectious agent, virus, or parasite), toxin (e.g., botulinum), or other poison (e.g., heavy metals such as lead and mercury, or chemical agents such as a nerve agent) in a municipal water supply, or may want to determine a bulk concentration of an irritant (e.g., pollen or smog), in the air. The bulk concentration is typically expressed as a ratio of the number of "pieces" (e.g., particles, molecules, cells, atoms) of the target per unit volume, or as a normalized ratio of the number of units of a volume occupied by the target to a reference number of units of the volume (e.g., parts per million).

FIG. 1 is a diagram that illustrates an example of an analog technique for determining a bulk concentration $\lambda_T$ of a target 10 in a source 12. For example, the target 10 may be the polio virus or bacteria (e.g., *E Coli* or other coliform bacteria) and the source 12 may be a municipal water supply.

Referring to FIG. 1, one or more samples 14 are taken from the source 12. For example, if the source 12 is a municipal water supply, then the sample 14 may be about 10 milliliters (mL) of water from a strategically selected location 16 (e.g., in the middle of the body of water, or near an input port where the water is drawn into a water-treatment facility).

Next, each sample 14 is treated with a substance, such as a reagent, that causes the sample to exhibit one or more phenomena each having a respective level related to the concentration of the target 10 in the sample. For example, a reagent added to a sample 14 can bind with the molecules of the target 10, and cause the sample to exhibit a color having an intensity, saturation, hue, or shade that is related to the concentration of the target in the sample, where the color can be caused by the bound reagent absorbing one or more wavelengths of light, luminescing one or more wavelengths of light, or absorbing one or more first wavelengths of light and luminescing one or more second wavelengths of light.

Then, a technician (not shown in FIG. 1) illuminates the sample with a light source designed for activating the reagent to exhibit a color.

Next, a human technician (not shown in FIG. 1) considers the one or more exhibited phenomena for one or more samples 14 and makes an estimation $\hat{\lambda}_T$ of the actual bulk concentration $\lambda_T$ of the target 10 in the source 12. For example, if a sample 14 exhibits a lighter shade of green (left end of a shade chart 16), then the technician estimates the bulk concentration $\lambda_T$ of the target 10 in the sample 12 as "low;" conversely, if the sample exhibits a darker shade of green (right end of the shade chart), then the technician estimates the bulk concentration $\lambda_T$ of the target 10 in the sample 14 as "high." The technician considers the respective shade of green of each of one or more additional samples 14, and, based on his/her perception of the shades of green, effectively averages the shades of green for all considered samples to arrive at a final estimate of the bulk concentration $\lambda_T$. For example, the technician may characterize the bulk concentration $\lambda_T$ as "high," "medium," "low," "dangerous," or "safe."

But a problem with this analog technique is that the technician cannot quantify, with any precision, his/her estimate $\hat{\lambda}_T$ of the bulk concentration $\lambda_T$ of the target 10 in the source 12. That is, with this analog technique, the technician can provide only a coarse, or "rough," estimate $\hat{\lambda}_T$ of the bulk concentration $\lambda_T$.

Unfortunately, a "rough" estimate $\hat{\lambda}_T$ of the bulk concentration $\lambda_T$ is insufficient for some applications.

In another analog technique, a technician (not shown in FIG. 1) compares each of one or more phenomena exhibited by one or more samples 14 to a respective chart, which quantifies the bulk concentration $\lambda_T$ of the target 10 in the source 12 relative to a level of a respective phenomenon, and makes an estimation $\hat{\lambda}_T$ of the bulk concentration $\lambda_T$ in response to the one or more charts. For example, the chart 16 includes four shades of green that are each associated with a corresponding value $\lambda_{T\_1}$-$\lambda_{T\_4}$ of the bulk concentration $\lambda_T$, where the association between a shade of green and corresponding value $\lambda_{T\_n}$ was previously determined using one or more test sources having known values of the bulk concentration $\lambda_T$ of the target 10. The technician compares the shade of each sample 14 with the four shades of green in the chart 16. If, per the example shown in FIG. 1, the shade of the sample 14 is between two of the shades (here the sample is between the two leftmost shades) in the chart 16, then, based on his/her perception of how "close" the shade of the sample is to each of the two shades, the technician interpolates the bulk concentration $\lambda_T$ as having an estimated value $\hat{\lambda}_{T\_Interpolated}$ that lies between the values $\lambda_{T\_1}$ and $\lambda_{T\_2}$ associated with the two shades in the chart (this color-shade interpolation is similar to the color-shade interpolation that one performs to determine the pH and alkalinity levels of water in a swimming pool or spa). The technician may compare, to the chart 16, the respective shade of green of each of one or more additional samples 14, and average the interpolated values of the bulk concentration obtained from all compared samples to arrive at a final estimated value $\hat{\lambda}_{T\_Interpolated}$ of the bulk concentration $\lambda_T$ of the target 10.

Although the latter analog technique may provide a more accurate estimate $\hat{\lambda}_T$ of the bulk concentration $\lambda_T$ of the target 10 in the source 12, this technique still depends on the abilities of a human technician to distinguish sometimes subtle differences in the shades of a color, or in the levels of one or more other phenomena.

FIG. 2 is a diagram that illustrates a digital technique for determining a bulk concentration $\lambda_T$ of a target 10 in a source 12.

A digital assay 20 is formed by dividing sample into compartments (also called droplets if the compartments are of a liquid) 22, each of which is small enough (e.g., ≤~100 picoliters (pL)) such that some compartments include the target 10, and some compartments do not include the target. The number of compartments 22 in the digital assay 20 can range from tens to thousands depending on the application and the amount of precision desired.

The technique is a digital technique because what is considered is whether a compartment 22 does include at least one target 10 (an "on" compartment) or does not include at least one target (an "off" compartment). For example, as described above in conjunction with FIG. 1, a reagent is added to each compartment 22, and binds to any molecule of the target 10 in the compartment (in this example, "at least one target" means at least one molecule of the target or, said another way, means at least one target molecule). If the compartment 22 turns any shade of green (i.e., the compartment includes at least one target), then the compartment is an "on" compartment; conversely, if the compartment does not turn green (i.e., the compartment lacks any target), then the compartment is an "off" compartment.

Algorithms exist for generating an estimate $\hat{\lambda}_T$ of the bulk concentration $\lambda_T$ of the target 10 in the source 12 in response to characteristics exhibited by a digital assay, the characteristics including the number of "on" compartments 22, the number of "off" compartments, and the aggregate volume of the compartments.

Because the volumes of the compartments 22 are relatively small, low-cost, portable equipment often generates the compartments having significantly different volumes, where the largest compartment volume in the digital assay 20 is, for example, approximately ten or more times the smallest compartment volume. A digital assay having compartments with such disparate volumes is called a "polydisperse digital assay."

Unfortunately, the accuracy of existing algorithms decreases dramatically as the uniformity of the compartment volumes decreases. Said another way, as the disparity among the compartment volumes increases, the accuracy of the estimated bulk concentration $\hat{\lambda}_T$ determined by existing algorithms decreases.

Consequently, for many applications, the disparity in the volumes of the compartments 22 generated by low-cost equipment is so large that existing algorithms cannot yield sufficiently accurate values of $\hat{\lambda}_T$.

Still referring to FIG. 2, to increase the accuracy of existing algorithms, specialized equipment has been developed to generate digital assays having compartments with more uniform volumes.

For example, a digital assay 30 has compartments 32 with approximately equal volumes, and such a digital assay is called a "monodisperse digital assay."

But although a monodisperse digital assay, such as the digital assay 30, significantly increases the accuracy with which existing algorithms can estimate the bulk concentration $\lambda_T$ of the target 10 in the source 12, the generation of a monodisperse digital assay is often beset by a number of problems.

For example, equipment for generating a monodisperse digital assay, such as the digital assay 30, can be expensive, bulky, and slow. Such equipment can cost US$150,000 or more; therefore, such equipment is often unattainable by charitable and other organizations with limited funds. Consequently, such organizations send out their samples to a lab for analysis, and typically wait a significant amount of time (e.g., a few weeks to a few months) for an estimate $\hat{\lambda}_T$ of the bulk concentration $\lambda_T$. Furthermore, such equipment can be on the order of 6 feet×6 feet×2 feet; therefore, it is often unsuitable for on-site applications (e.g., on the bank of a reservoir, at a well for drinking water). Consequently, even if an organization owns, or otherwise has access to, such equipment, transporting the sample from the source to the equipment increases the time for, and the cost of, obtaining an estimate $\hat{\lambda}_T$ of the bulk concentration $\lambda_T$. Moreover, such equipment can take a relatively long time, e.g., on the order of one minute, to generate each compartment of a monodisperse digital assay. Consequently, because a monodisperse digital assay may include tens, hundreds, or even thousands of compartments, the throughput of such equipment is limited, and, therefore, increases the time for, and the cost of, obtaining an estimate $\hat{\lambda}_T$ of the bulk concentration $\lambda_T$.

Therefore, a need has arisen for a system that is smaller, less expensive, and faster than existing equipment, yet that is at least as accurate as existing systems.

In an embodiment, such a system includes a compartment-generating device, a compartment detector, and electronic computing circuitry. The device is configured to generate compartments of a digital assay, at least one of the compartments having a respective volume that is different from a respective volume of each of at least another one of the compartments. The detector is configured to determine a number of the compartments each having a respective concentration of a target that is greater than a threshold concentration. And the electronic circuitry is configured to determine a bulk concentration of the target in a source of the sample in response to the number.

Compared to equipment for generating a monodisperse digital assay, such a system can be portable, lower-cost, and faster, yet can yield similar accuracy. In an embodiment, these improvements flow from the system being configured to implement an algorithm that allows for accurately estimating the bulk concentration $\lambda_T$ of a target in a source from a polydisperse digital assay.

DETAILED DESCRIPTION

The words "approximately," "substantially," "about," and similar words and phrases, are used below to indicate that a quantity can be in range of ±10% of a value given for the quantity, and that two or more quantities can be exactly equal, or can be within ±10% of each other. Furthermore, use of such a word to describe a range b to c indicates a range of $b-10\% \cdot |c-b|$ to $c+10\% \cdot |c-b|$.

Figure 3:
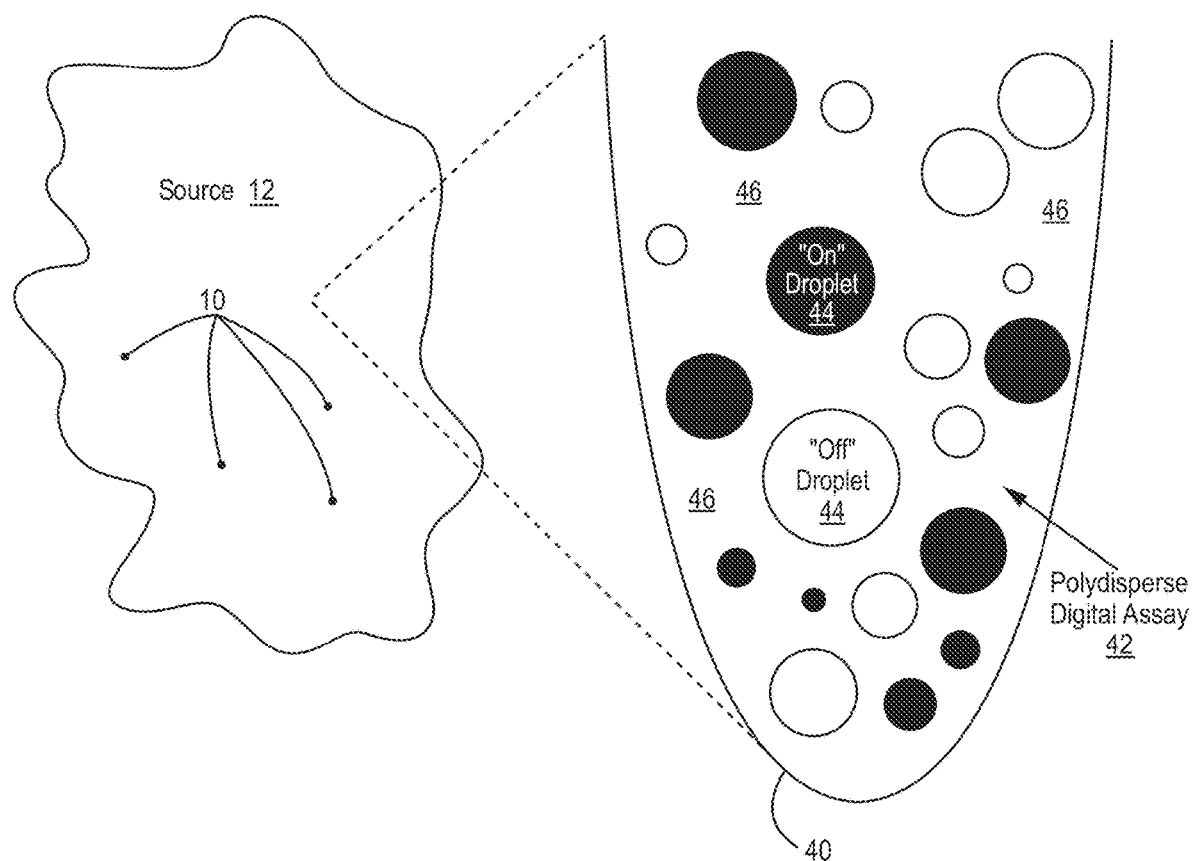
FIG. 3 is a diagram that illustrates a digital technique for determining a bulk concentration of a target in a source, according to an embodiment.

FIG. 3 is a diagram that illustrates a digital technique for determining a bulk concentration $\lambda_T$ of a target 10 in a source 12, according to an embodiment. For example, one can use the digital technique to obtain an accurate estimate $\hat{\lambda}_T$ of the bulk concentration $\lambda_T$.

A container 40, such as a clear test tube of glass or plastic, holds a polydisperse digital assay 42 of compartments 44 suspended in a barrier phase 46, according to an embodiment in which a dark compartment is "on" and a light compartment is "off." In the described example, each compartment 44 is a respective droplet of a liquid, such as water, and the barrier phase 46 is another liquid, such as an oil, in which the droplets are suspended. The combination of the droplets 44 and the liquid barrier phase 46 is an emulsion.

Figure 4:
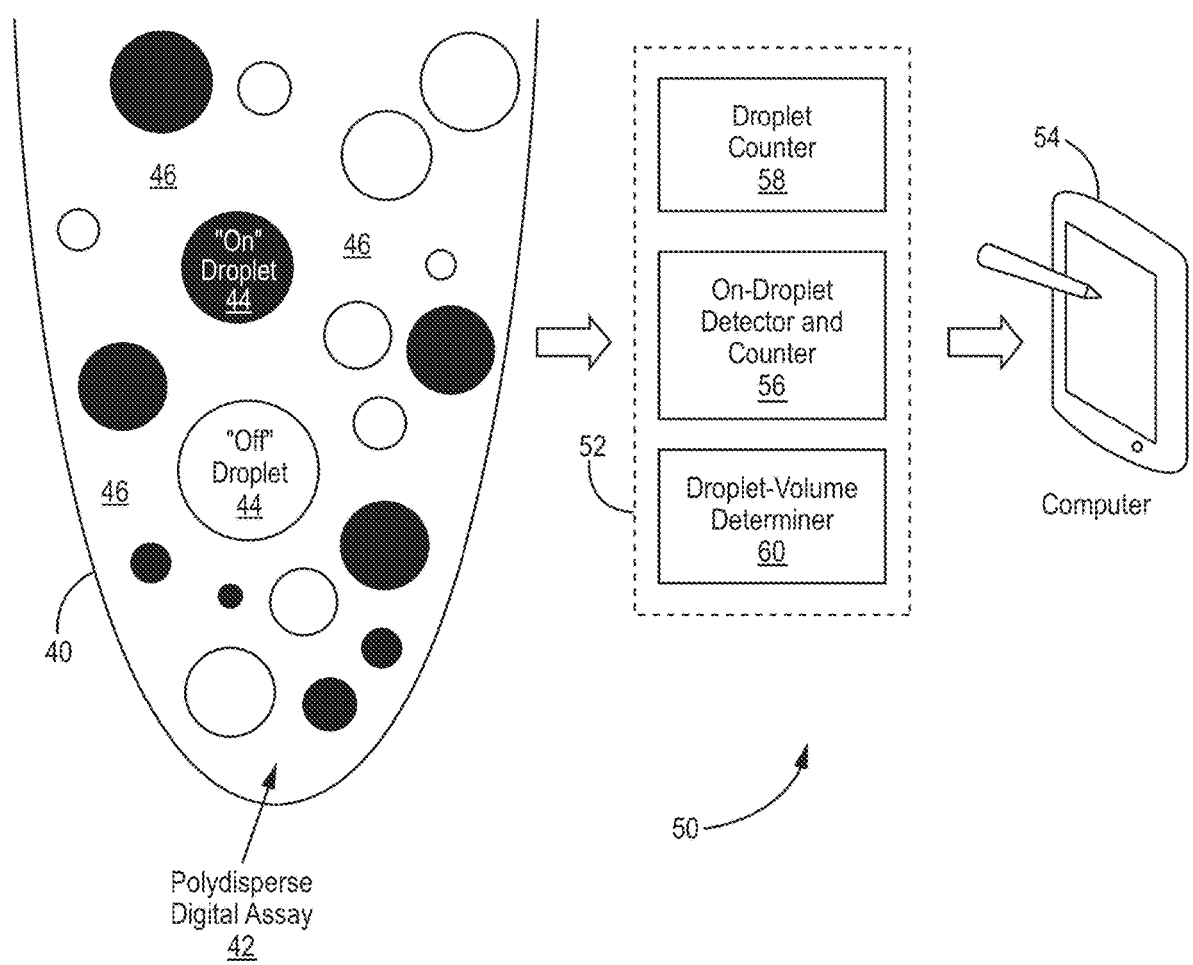
FIG. 4 is a diagram of a system configured to implement the digital technique illustrated by FIG. 3, according to an embodiment.

FIG. 4 is a diagram of the container 40, the polydisperse digital assay 42 and the barrier phase 46 within the container, and a system 50 configured to determine the bulk concentration $\lambda_T$ of the target 10 (FIG. 3) in the source 12 (FIG. 3) in response to at least some of the droplets 44 of the polydisperse digital assay, according to an embodiment.

The system 50 includes a droplet analyzer 52 and a computing device 54. Both the droplet analyzer 52 and computing device 54 include electronic circuitry that is hardwired, or is configured by software or firmware, to perform the respective functions and operates described below.

The droplet analyzer 52 includes an "on"-droplet detector and counter 56, a droplet counter 58, and a droplet-volume determiner 60. The "on"-droplet detector and counter 56 includes electronic circuitry and one more optical sensors configured to detect, and to determine the number of, "on" droplets 44 in the polydisperse digital assay 42. The droplet counter 58 includes electronic circuitry and one or more optical sensors (one or more of which may be shared with the on-droplet detector and counter 56) configured to determine the total number of "on" and "off" droplets 44 in the polydisperse digital assay 42. And the droplet-volume detector 60 includes electronic circuitry and one or more optical sensors (one or more of which may be shared with the "on"-droplet detector and counter 56 or the droplet counter 58) configured to measure, or otherwise to determine, the respective volume of each of the droplets 44.

The computing device 54 can be any suitable computer, such a laptop, a tablet, or a smart phone, that includes one or more microprocessors or microcontrollers.

Figure 5:
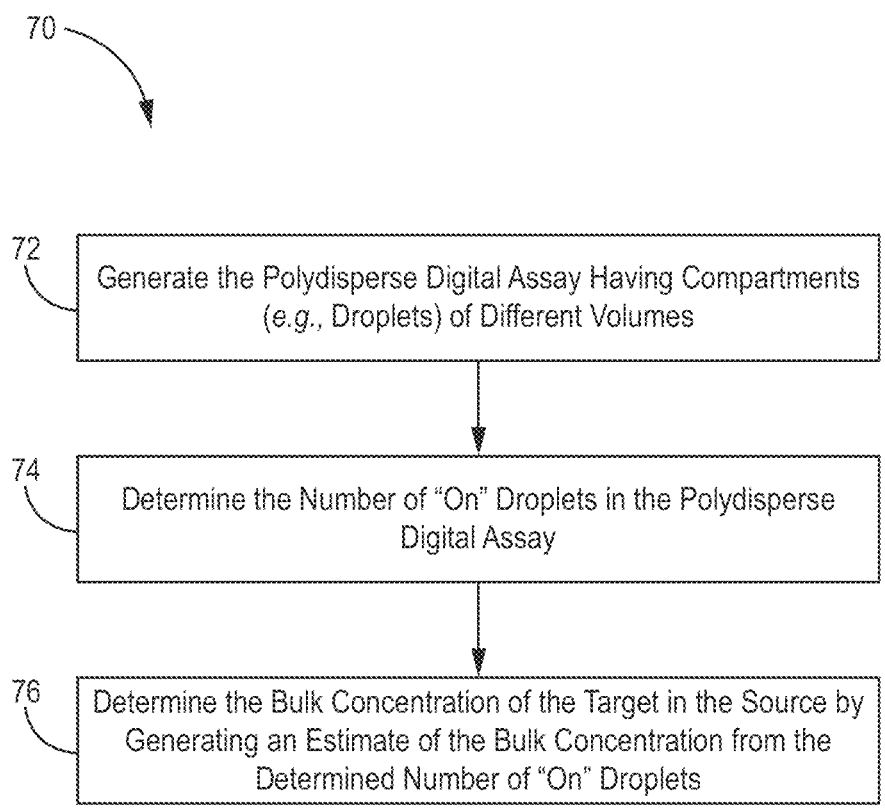
FIG. 5 is a flow chart of the digital technique illustrated by FIG. 3 and implemented by the system of FIG. 4, according to an embodiment.

FIG. 5 is a flow chart 70 of an algorithm for determining a bulk concentration $\lambda_T$ of a target 10 in a source 12, according to an embodiment.

Referring to FIGS. 3-5, the algorithm represented by the flow chart 70, and operation of the system 50 while implementing the algorithm, are described, according to an embodiment in which both the compartments 44 and the barrier phase 46 are liquids such that the compartments 44 are droplets suspended in the liquid barrier phase.

Figure 1:
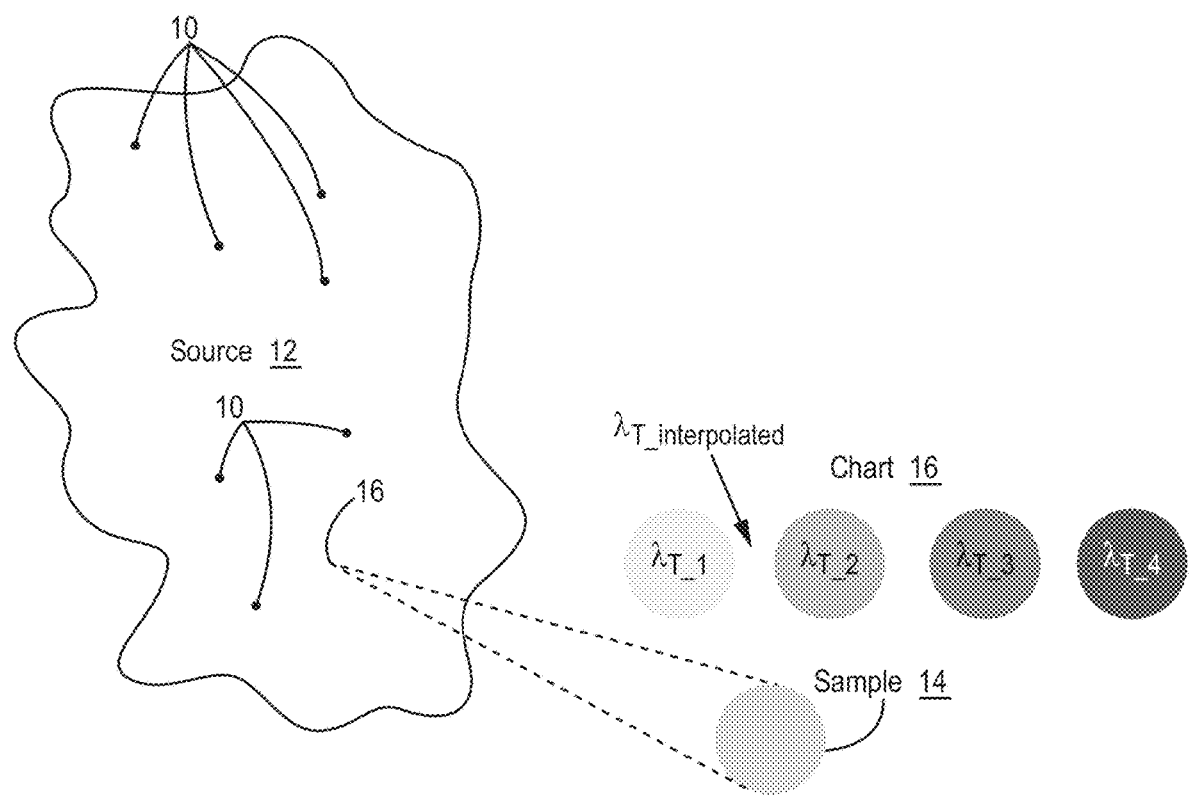
FIG. 1 is a diagram that illustrates an analog technique for determining a bulk concentration of a target in a source.
Figure 2:
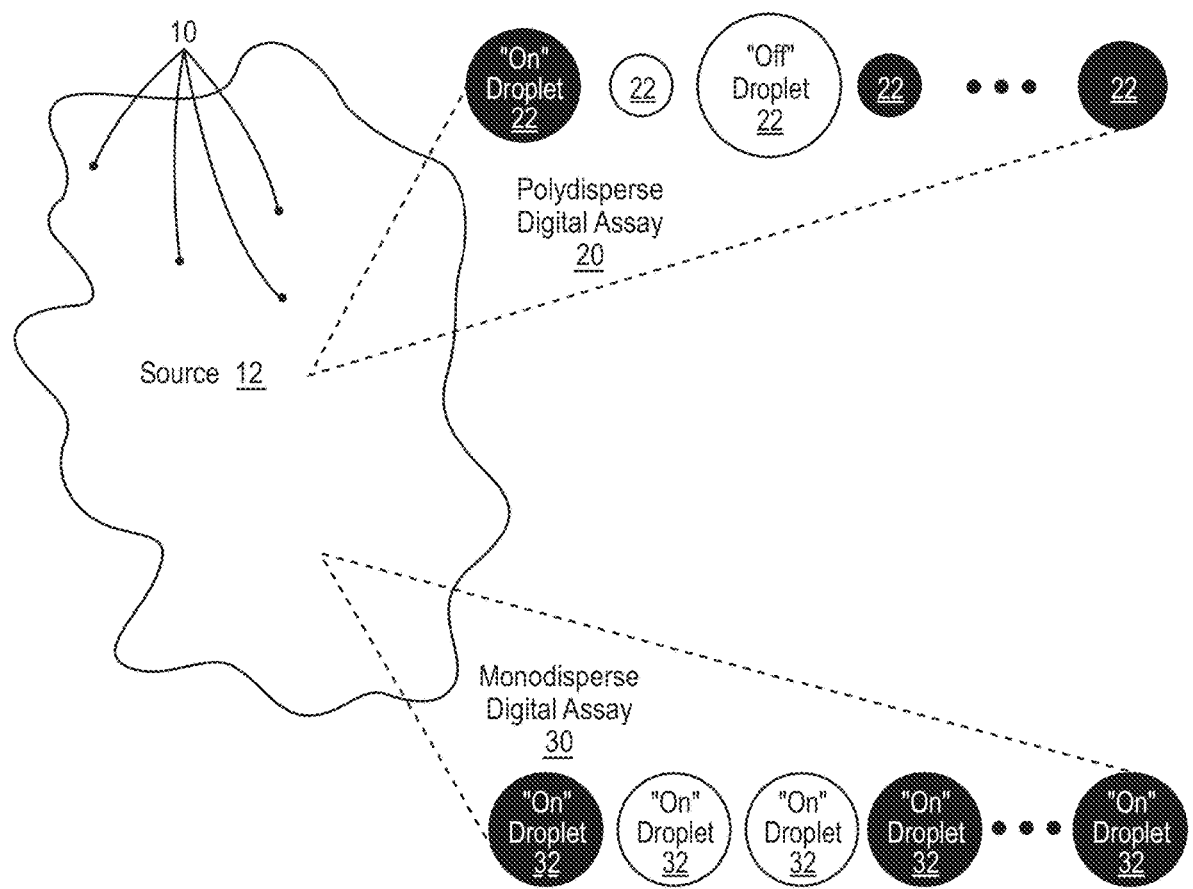
FIG. 2 is diagram that illustrates two digital techniques for determining a bulk concentration of a target in a source.

First, at a step 72, a technician (not shown in FIGS. 3-5) generates the droplets 44 of different volumes (e.g., in a range of approximately 1 pL-100s pL) from a sample of the source 12 to form the polydisperse digital assay 42. For example, the technician adds an indicated volume of the barrier-phase liquid 46, such as an oil, to the container 40, adds an indicated sample volume of the source 10 to the barrier-phase liquid in the container, plugs the top of the container, and shakes the container to form an emulsion of the droplets 44 suspended in the barrier-phase liquid. Further in example, the container 40 includes a measurement line (not shown in FIGS. 3-5) to indicate the volume of the barrier-phase liquid to be added, and the technician uses a measurement device, such as an "eye" dropper, to obtain and measure the volume of the sample. Alternatively, the container 40 may include another measurement line (not shown in FIGS. 3-5), higher up on the container than the barrier-phase measurement line, to indicate the volume of the sample to be added after the barrier-phase liquid is added. Still further in example, the technician adds to the container 40, before the technician shakes it, a reagent for rendering target-carrying droplets 44 luminescent as described above in conjunction with FIGS. 1-2. Using this "shake-and-bake" technique, the technician can generate the polydisperse digital assay 42 in a matter of a few ones to tens of seconds, and in no more than a few minutes even if the time for setting up the system 50 and obtaining the sample is included.

Next, at a step 74, the "on"-droplet detector and counter 56 determines the number a of "on" droplets 44 in the polydisperse digital assay 42. For example, the counter 56 can include a combination illumination device and image-capture device, such as a light source and a small camera, which the technician holds up near, or against, the container 40. The illumination device illuminates the droplets 44 so that droplets including the target luminesce a color having shades respectively corresponding to the concentrations of the target in the droplets. The technician then presses a button on the device, or a virtual button displayed by the computer 54, to capture an image of the droplets 44 in the container while the droplets including the target are luminescing. Using conventional image-processing techniques, the computer 54 analyzes the image, detects the droplets 44, and determines whether each detected droplet 44 is "on" or "off" by determining, for each droplet, whether the number of targets (or, said another way, the number of the target) within the droplet exceeds a threshold number (e.g., one target molecule, five target molecules, ten target molecules). For example, an optical signal that the target luminesces has a property (e.g., intensity, color, color shade) indicative of the number of targets within a droplet 44, and the computer 54 determines whether the number of targets within the droplet exceeds the threshold number by determining whether the property of the target-related optical signal exceeds (or is below) a signal-property threshold. Further in example, the computer 54 compares a shade of the color (e.g., green), or an opacity, of a droplet 44 to a threshold shade or opacity, determines that the droplet is "on" if the level of the shade or opacity is greater than or equal to the threshold, and determine that the droplet is "off" if the level of the shade or opacity is less than the threshold. Alternatively, the technician uses the "on"-droplet detector and counter 56 to capture multiple images of the droplets 44 from different orientations relative to the container 40 so that the computer 54 is able to detect droplets that might otherwise be obscured by other droplets in a single image.

Then, at a step 76, the computer 54 generates an estimate $\hat{\lambda}_T$ of the bulk concentration $\lambda_T$ of the target 10 in the source 12 in response to the number a of "on" droplets 44 in the container 40. For example, as described below in conjunction with FIG. 6, the computer 54 executes one or more equations to solve for $\hat{\lambda}_T$ in response to a.

The system 50, and the algorithm that the system implements, provide one or more advantages over existing systems and techniques for determining a bulk concentration of a target in a source. For example, the container 40 and the barrier phase 46 are configured to provide inexpensive, on-site, and fast generation of the digital assay 42. Furthermore, the system 50 is configured to provide inexpensive, on-site, and fast estimation of the bulk concentration $\lambda_T$ of the target 10 in the source 12 even in response to a polydisperse digital assay 42 having compartments 44 of disparate volumes.

Still referring to FIGS. 3-5, alternate embodiments of the system 50 and of the above-described algorithm are contemplated. For example, one or more steps can be added to the algorithm, and one or more of the above-described steps can be omitted from the algorithm. Furthermore, one or more components can be added to the system 50, and one or more of the above-described components can be omitted from the system. Moreover, use of a reagent may be omitted if, for example, the target luminesces without the reagent, or if the system 50 can determine, in a manner that does not involve use of a reagent, whether the number of targets in a compartment 44 exceeds the threshold number by determining whether a property of a target-related signal (e.g., color, color shade) exceeds a signal-property threshold. In addition, the computer 54 may perform one or more functions and operations attributed to the droplet analyzer 52, and the droplet analyzer may perform one or more functions and operations attributed to the computer. Furthermore, a cloud server may complement, or replace, the computer 54. Moreover, the system 50 and the above-described algorithm yield similar results and advantages for a monodisperse digital assay. In addition, embodiments described below in conjunction with FIGS. 6-10 may be applicable to the system 50 and to the above-described algorithm.

Figure 6:
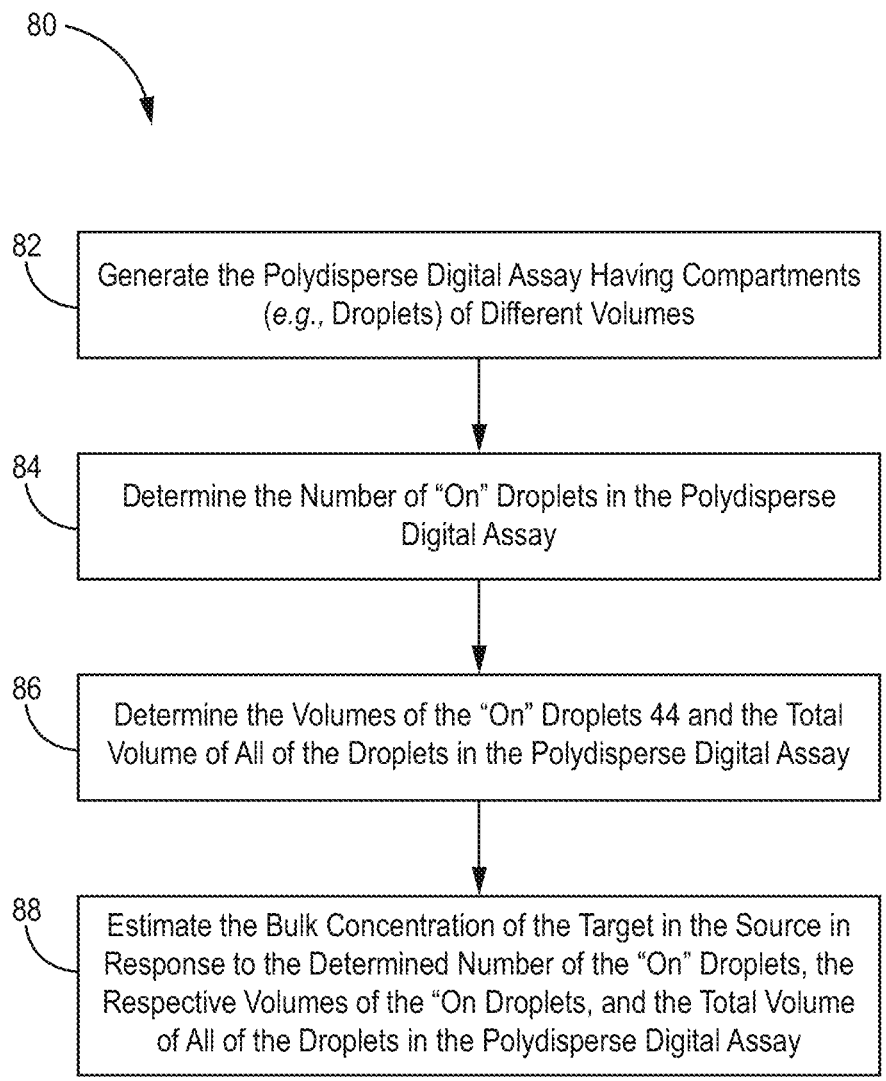
FIG. 6 is a flow chart of the digital technique illustrated by FIG. 3 and implemented by the system of FIG. 4, according to another embodiment.

FIG. 6 is a flow chart 80 of a digital-variable-volume (DVV) algorithm for determining a bulk concentration $\lambda_T$ of a target 10 (FIG. 3) in a source 12 (FIG. 3), according to an embodiment. The DVV algorithm is suitable for situations in which the system 50 includes the droplet-volume determiner 60, or in which the respective volumes of the "on" droplets 44, and the aggregate volume of all the droplets, otherwise can be determined.

Referring to FIGS. 3-4 and 6, the DVV algorithm represented by the flow chart 80, and operation of the system 50 while implementing the algorithm, are described according to an embodiment in which both the compartments 44 and the barrier phase 46 are liquids such that the compartments 44 are droplets suspended in the barrier phase to form an emulsion.

First, at a step 82, a technician (not shown in FIGS. 3-4 and 6) generates the droplets 44 of disparate volumes (e.g., in a range of approximately 1 pL-100s pL) from a sample of the source 12 to form the polydisperse digital assay 42. For example, the technician may form the polydisperse digital assay 42 using a method that is the same as, or that is similar to, the "shake-and-bake" method described above in conjunction with step 72 of FIG. 5.

Next, at a step 84, the "on"-droplet detector and counter 56 determines the number a of "on" droplets 44 in the polydisperse digital assay 42. For example, the "on"-droplet detector and counter 56 may determine the number a using a method that is the same as, or that is similar to, the method described above in conjunction with step 74 of FIG. 5.

Then, at a step 86, the droplet-volume determiner 60 determines the respective volume $v_i$ of each of the detected "on" droplets 44, and, if necessary, determines the aggregate volume $V_{Total}$ of the droplets 44 by summing the respective volumes of the detected "on" and "off" droplets. For example, to determine the respective volume $v_i$ of each of the a "on" droplets 44, the determiner 60 analyzes the one or more images that the system 50 captured at the step 84 using a conventional droplet-volume-determining algorithm. To determine the aggregate volume $V_{Total}$, the determiner 60 also determines the volumes of the "off" droplets 44 in the same way that the determiner determines the volumes $v_i$ of the "on" droplets, sums the volumes of the "off" droplets with the volumes $v_i$ of the "on" droplets, and sets $V_{Total}$ equal to the determined sum. Alternatively, the droplet-volume determiner 60 is configured to operate as described above but is part of, or is otherwise included in, the computer 54 instead of the droplet analyzer 52. In yet another alternative, because the aggregate volume of the sample is the same as the aggregate volume $V_{Total}$ of the droplets 44, and because the volume of the sample is known per step 82, the technician enters into the computer 54 the volume of the sample, and the computer sets $V_{Total}$ equal to the entered sample volume.

Next, at a step 88, the computer 54 solves for the estimated bulk concentration $\hat{\lambda}_T$ of the target 10 in the source 12 according to the following equation:

$$\sum_{i=1}^{a} \frac{v_i}{1 - e^{-v_i \hat{\lambda}_T}} = V_{Total} \qquad (1)$$

A derivation and explanation of equation (1) is included below.

In an ideal example, each "on" droplet 44 would contain one and only one of the target such that the computer 54 could determine the estimated bulk concentration $\hat{\lambda}_T$ from the number a of "on" droplets 44 divided by the volume $V_{Total}$ of the sample 14, where a would also equal the number of targets in the sample.

But because in an actual, non-ideal, example each "on" droplet 44 may contain more than one of the target 10, determining the estimated bulk concentration $\hat{\lambda}_T$ from a/$V_{Total}$ may lead to an error caused by an undercounting of the number of the target in the sample 14.

To reduce or eliminate such an undercounting error where the respective number of the target in one or more of the "on" droplets 44 of the sample 14 is unknown, the computer 54 is configured to use equation (1) to estimate the bulk concentration $\lambda_T$ of the target in the source 12.

For each "on" droplet 44, equation (1) includes a respective expression for the probability that the droplet includes at least one of the target, the probability being dependent on, and, therefore, the respective expression including, the respective volume of the droplet.

Consequently, equation (1) not only effectively accounts for the possibility that each of one or more of the "on" droplets 44 contains more than one of the target 10, equation (1) also effectively accounts for a larger "on" droplet 44 being more likely than a smaller "on" droplet to contain more than one of the target.

The system 50, and the DVV algorithm that the system 50 is configured to implement, provide one or more advantages over existing systems and techniques. For example, the container 40 and binary phase 46 provide for inexpensive, on-site, and fast generation of the digital assay 42. Furthermore, the system 50 provides for inexpensive, on-site, fast, and accurate estimation of a bulk concentration $\lambda_T$ of a target 10 in a source 12 even in response to a polydisperse digital assay 42 having droplets 44 of disparate volumes.

Still referring to FIGS. 3-4 and 6, alternate embodiments of the system 50 and the DVV algorithm are contemplated. For example, instead of the "on"-droplet detector and counter 56 determining the number a of "on" droplets 44, the technician may count the number a of "on" droplets and enter the number a into the computer 54. Moreover, instead of the droplet-volume determiner 60 determining the volumes $v_i$ of the "on" droplets 44, the technician may use a device, such as a ruler or microscope, to estimate the volumes $v_i$, and then enter these volumes into the computer 54. Moreover, the system 50 and the above-described algorithm yield similar results and advantages for a monodisperse digital assay. In addition, alternate embodiments described above in conjunction with FIGS. 3-5 and below in conjunction with FIGS. 7-11 may be applicable to the system 50 and the DVV algorithm.

Figure 7:
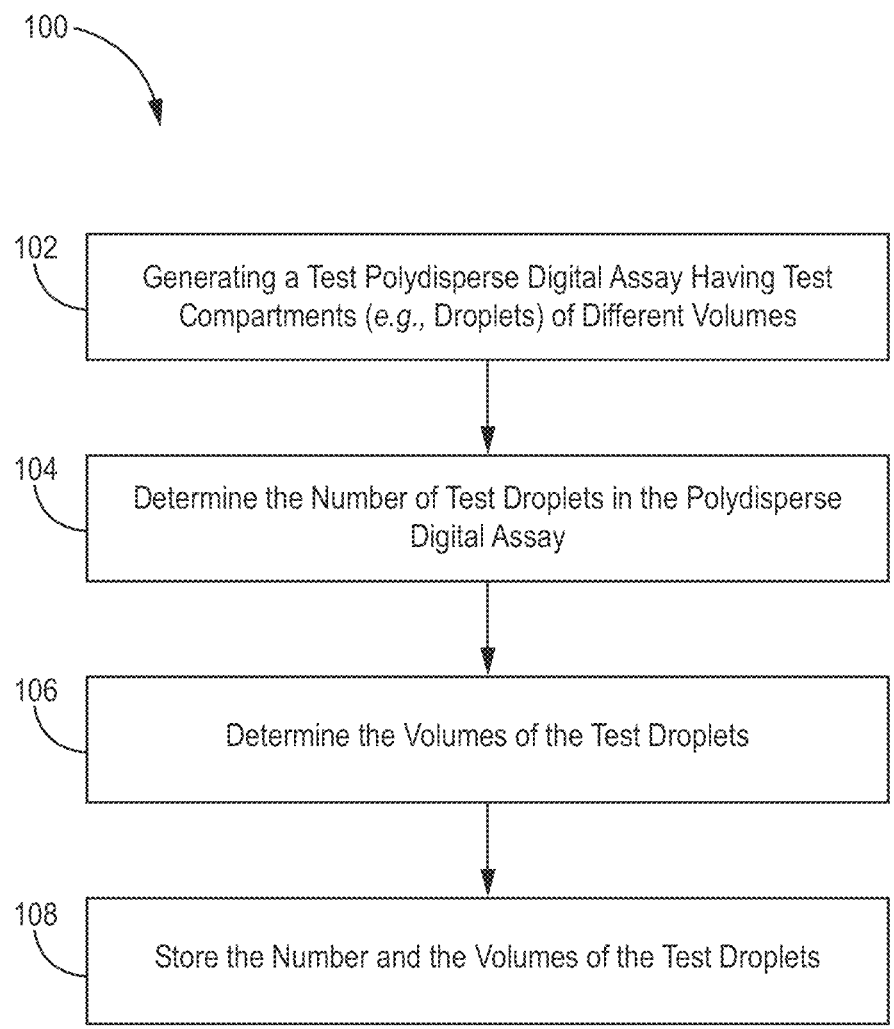
FIG. 7 is a flow chart of a technique for characterizing the polydisperse digital assay of FIGS. 3-4, according to an embodiment.

FIG. 7 is a flow chart 100 of an algorithm for characterizing the volumes of the compartments (e.g., droplets) 44 generated with the container 40 and barrier phase 46 of FIG. 4, according to an embodiment.

Figure 8:
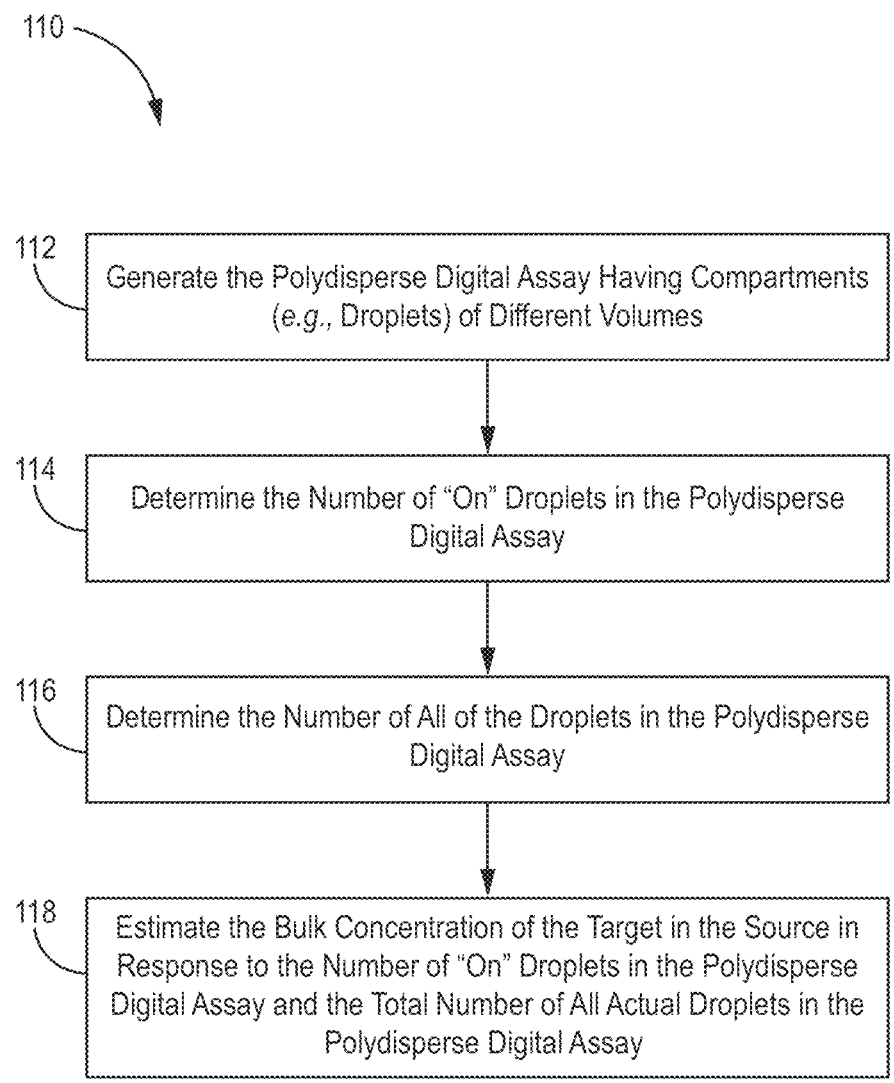
FIG. 8 is a flow chart of the digital technique illustrated by FIG. 3 and implemented by FIG. 4, according to yet another embodiment.

FIG. 8 is a flow chart 110 of a digital-variable-volume-approximation (DVVA) algorithm for determining a bulk concentration $\lambda_T$ of a target 10 (FIG. 3) in a source 12 (FIG. 3), according to an embodiment. The DVVA algorithm is suitable for situations in which the system 50 lacks the droplet-volume determiner 60, or in which the respective volumes of the "on" droplets 44, and the aggregate volume of all the droplets, are otherwise unknown.

Referring to FIGS. 3-4 and 7, the compartment-volume characterizing algorithm is described, according to an embodiment in which the compartments 44 are droplets.

At a step 102, a technician (not shown in FIG. 3-4 or 7) generates a set of test droplets of different volumes (e.g., in a range of approximately 1 pL-100 pL) from a test sample that is similar to a sample of the source 12 of FIG. 3 to form a test polydisperse digital assay; for example, if the intended source 12 is a body of water, then the technician may use a sample of water. The technician adds an indicated volume of the barrier-phase liquid 46, such as an oil, to the container 40, adds an indicated volume of the test sample to the barrier-phase liquid in the container, plugs the top of the container, and shakes the container to form an emulsion of test droplets suspended in the barrier-phase liquid. The container 40 may include a measurement line (not shown in FIG. 3-4 or 7) to indicate the volume of the barrier-phase liquid to be added, and the technician may use a measurement device, such as an "eye" dropper, to add an indicated volume of the test sample. Alternatively, the container may include another measurement line (not shown in FIG. 3-4 or 7), higher up on the container than the barrier-phase measurement line, to indicate the volume of the test sample to be added after the barrier-phase liquid is added.

Next, at a step 104, the droplet counter 58, or a similar counter, determines the number m of test droplets, and at a step 106, the droplet-volume determiner 60, or a similar determiner, determines a respective volume $v_{i\_characterized}$ for each of the m test droplets.

Then, at a step 108, the computer 54 stores the number m of test droplets, and stores the volumes $v_{i\_characterized}$ of the test droplets, in a memory (not shown in FIG. 3). Alternatively, the number m and the corresponding volumes $v_{i\_characterized}$ can be stored in another memory from which the computer 54 is configured to download the values of m and $v_{i\_characterized}$.

The theory behind generating the characterized number m and the characterized volumes $v_{i\_characterized}$ is that similar containers, sample substances, and barrier phases will generate similar values for m and $v_{i\_characterized}$ such that the values of m and $v_{i\_characterized}$ can be used to determine a bulk concentration $\lambda_T$ of the target 10 (FIG. 3) in the sample 12 (FIG. 3) in situations where the volumes $v_i$ of the actual droplets 44 cannot be determined or are otherwise unknown. That is, the statistical dependence between the actual droplet volumes $v_i$ and the characterized droplet volumes $v_{i\_characterized}$ is high enough that, as described below, the number m and volumes $v_{i\_characterized}$ of the test droplets can be used to determine the actual bulk concentration $\lambda_T$ of the target 10 in the source 12 in a situation where the volumes $v_i$ of the actual droplets 44 are unknown.

Still referring to FIG. 7, alternative embodiments of the droplet-characterization algorithm are contemplated. For example, the steps 102-106 can be repeated any suitable number of times to generate sets of test values for m and $v_{i\_characterized}$, and the computer 54, or a similar computer, can calculate the final values of m and $v_{i\_characterized}$ by interpolating values from one or more of the sets of test values.

Referring to FIGS. 3-4 and 8, the DVVA algorithm represented by the flow chart 110, and operation of the system 50 while implementing the DVVA algorithm, are described according to an embodiment in which both the compartments 44 and the barrier phase 46 are liquids such that the compartments 44 are droplets suspended in the barrier phase to form an emulsion.

First, at a step 112, a technician (not shown in FIGS. 3-4 and 8) generates the droplets 44 of disparate volumes (e.g., in a range of approximately 1 pL-100 pL) from a sample of the source 12 to form the polydisperse digital assay 42. For example, the technician may form the polydisperse digital assay 42 using a method that is the same as, or similar to, the "shake-and-bake" method described above in conjunction with step 72 of FIG. 5.

Next, at a step 114, the "on"-droplet detector and counter 56 determines the number a of "on" droplets 44 in the polydisperse digital assay 42. For example, the on-droplet detector and counter 56 may determine the number a using a method that is the same as, or similar to, the method described above in conjunction with step 74 of FIG. 5.

Then, at a step 116, the droplet counter 58 determines the number n of all droplets 44 (i.e., the sum of the "on" and "off" droplets) in the polydisperse digital assay 42 in the container 40. For example, to determine the number n of all droplets 44, the droplet counter 58 analyzes the one or more images that the system 50 captured at the step 114 using a conventional droplet-counting algorithm. Alternatively, the droplet counter 58 counts only the number b of "off" droplets 44, and adds this number to the number a of "on"

droplets, to generate n=a+b. Alternatively, the droplet counter 58 operates in a similar manner but is part of, or is included in, the computer 54 instead of being part of, or included in, the droplet analyzer 52.

Next, at a step 118, the computer 54 solves for the estimated bulk concentration $\hat{\lambda}_T$ of the target 10 in the source 12 according to the following equation:

$$\frac{1}{m}\left(\sum_{i=1}^{m} e^{-v_{i\_characterized}\hat{\lambda}_T}\right) - 1 + \frac{a}{n} = 0 \quad (2)$$

where m is the characterized number of droplets and each $v_{i\_characterized}$ is the characterized volume of a respective one of the m droplets as described above in conjunction with FIG. 7.

A derivation and explanation of equation (2) is included below.

The system 50, and the DVVA algorithm that the system is configured to implement, provide one or more advantages over existing systems and techniques. For example, the container 40 and barrier phase 46 provide for inexpensive, on-site, and fast generation of the digital assay 42. Furthermore, the system 50 provides for inexpensive, on-site, and fast estimation of a bulk concentration $\lambda_T$ of the target 10 in the source 12 even in response to a polydisperse digital assay 42 having droplets 44 of disparate volumes that are unknown.

Still referring to FIGS. 3-4 and 8, alternate embodiments of the system 50 and the DVVA algorithm are contemplated. For example, from the number m and volumes $v_{i\_characterized}$ of the test droplets described above in conjunction with FIG. 7, one may determine the probability density function $f(v)$ of the volumes of the test droplets, and solve for the estimated bulk concentration $\hat{\lambda}_T$ of the target 10 in the source 12 according to the following equation:

$$\frac{a}{n} = 1 - \int_{-\infty}^{\infty} e^{-\hat{\lambda}_T v} f(v) dv \quad (3)$$

Moreover, alternate embodiments described above in conjunction with FIGS. 3-7 and below in conjunction with FIGS. 9-11 may be applicable to the system 50 and the DVVA algorithm.

Figure 9:
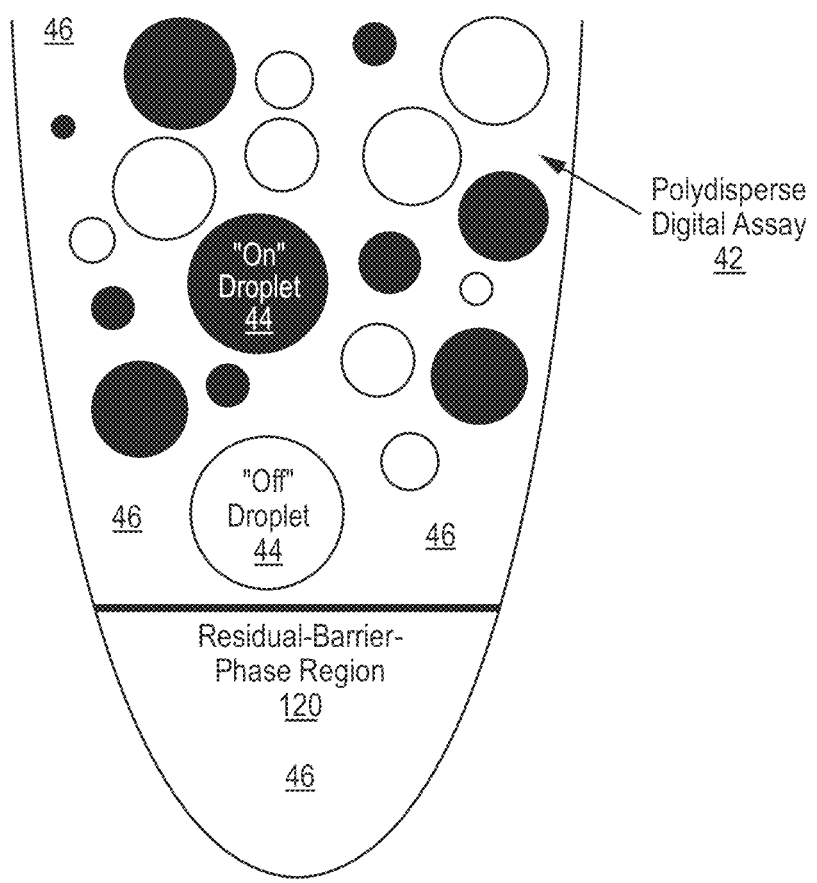
FIG. 9 is a diagram of a polydisperse digital assay and a residual barrier phase, according to an embodiment.

FIG. 9 is a diagram of the polydisperse digital assay 42 in the container 40, according another embodiment.

If the barrier phase 46, e.g., an oil, has a higher density than the droplets 44, then the droplets may "float" over a residual region 120 of the barrier phase that is devoid of droplets as shown in FIG. 9.

Conversely, if the barrier phase 46, e.g., an oil, has a lower density than the droplets 44, then the droplets may "sink" to the bottom of the container 40 such that the residual region 120 of the barrier phase that is devoid of droplets "floats" over the droplets (the residual region "floating" over the droplets is not shown in FIG. 9).

Figure 10:
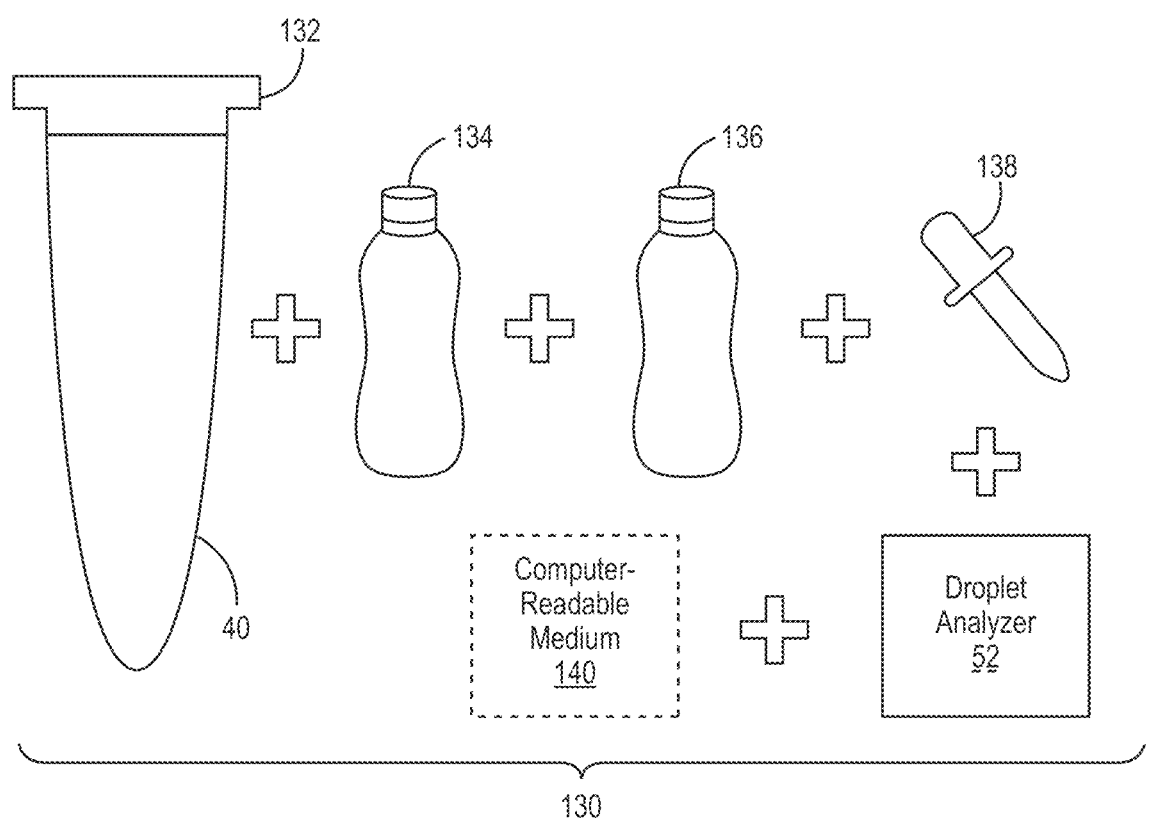
FIG. 10 is a diagram of a portable kit for determining a bulk concentration of a target in a source using the digital technique illustrated by FIG. 3, according to an embodiment.

FIG. 10 is a diagram of a digital-assay-generator-and-analyzer kit 130, according to an embodiment. The combination of the kit 130, a portable computer (e.g., laptop, tablet, smart phone), and one or more of the algorithms described above in conjunction with FIGS. 5-8 provides for inexpensive, on-site, and fast generation of the digital assay 42, and provides for inexpensive, on-site, and fast estimation of a bulk concentration $\lambda_T$ of a target 10 (FIG. 3) in a source 12 (FIG. 3) in spite of the polydisperse digital assay having droplets 44 of disparate volumes that may be unknown. For example, the kit 130 may cost approximately $30-$100, the amount of the barrier phase 46 required to generate each digital assay 42 may cost approximately $1 or less, the combined weight of the kit 130 and the computer 54 may be approximately 3 pounds (lbs.) to 10 lbs., and the total test time (from collection of a sample 14 to the computer 54 rendering an estimated bulk concentration $\hat{\lambda}_T$) may be approximately 20 minutes to 80 minutes.

In addition to the container 40 and the droplet analyzer 52, the kit 130 includes a container stopper 132, a re-openable and re-closable package (e.g., a screw-top bottle) 134 of the barrier phase 46, a re-openable and re-closable optional package (e.g., a screw-top bottle) 136 of a reagent, a dropper 138, and a non-transitory computer-readable medium 140. The stopper 132 is configured to form a liquid-tight seal at the opening of the container 40 to allow shaking of the container to form the polydisperse digital assay 42. The dropper 138 allows a technician to transfer the barrier phase 46 and the reagent from their respective packages 134 and 136 to the container 40, and allows a technician to obtain a liquid sample (e.g., water) from a source (e.g., reservoir) and to transfer the sample to the container. And the computer-readable medium is a suitable non-volatile memory that stores program instructions that, when executed by a portable computer, cause the computer to implement one of the algorithms described above in conjunction with FIGS. 5-8.

Still referring to FIG. 10, alternate embodiments of the kit 130 are contemplated. For example, the kit 130 may include a carrying case in which all of the other system components may be stored and carried. Furthermore, embodiments describe above in conjunction with FIGS. 1-9 and below in conjunction with FIG. 11 may be applicable to the kit 130.

Figure 11:
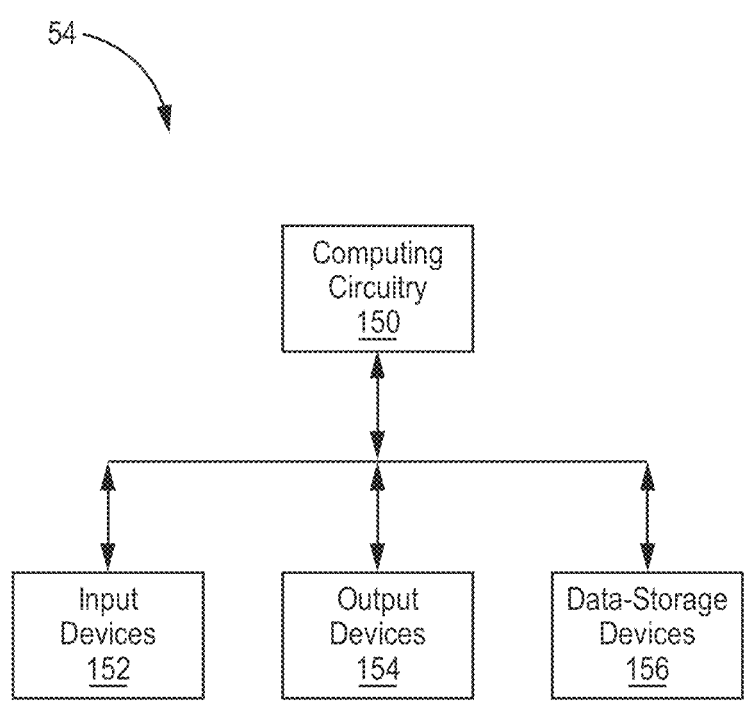
FIG. 11 is a diagram of the computer of FIG. 4, according to an embodiment.

FIG. 11 is a block diagram of the computer 54 of FIG. 4, according to an embodiment.

The computer 54 includes computing circuitry 150, one or more input devices 152, one or more output devices 154, and one or more data-storage devices 156.

The computing circuitry 150 includes circuitry that is configured to perform various functions and operations, such as the functions and operations described above in conjunction with FIGS. 3-8 and 10. For example, the computing circuitry 150 includes a microprocessor or microcontroller that is hardwired or configured with firmware, or that executes software, to perform the above-described functions and operations.

The one or more input devices 152 are configured to allow an operator or device to provide data or other information or signals to the computer 54. Examples of an input device 152 include a keyboard, mouse, touch screen, audible or voice-recognition component, the droplet analyzer 52 (FIG. 4), and so on The one or more output devices 154 are configured to provide data from the computing circuitry 150 to an operator or device in a suitable form, or to perform a function or operation under control of the computing circuitry 150. Examples of an output device 154 include a printer, video display, audio output components, the droplet analyzer 52 (FIG. 4), and so on.

The one or more data-storage devices 156 are configured to store data on or to retrieve data from volatile or non-volatile storage media (not shown). Examples of a data-storage device 156 include a magnetic disk, a FLASH memory, other types of solid state memory such as a random-access memory (RAM, SRAM, DRAM, USB "stick"), a ferro-electric memory, a tape drive, an optical disk like a compact disk and a digital versatile disk (DVDs), and so on.

Still referring to FIG. 11, alternate embodiments of the computer 54 are contemplated. For example, the computer 54 may omit one or more of the above-described devices, and may include one or more other devices.

Derivation and Explanation of Equations (1) and (2)

General Definitions and Assumptions

In digital assays, the targets (molecules, cells, etc.) in the bulk sample are randomly distributed into many compartments. A compartment with one or more targets gives a signal (e.g., fluorescent intensity after nucleic acid amplification), and is called an "on" compartment. A compartment without targets does not provide a signal, and is called an "off" compartment. Targets are distributed into compartments following the Poisson distribution. An assay system, such as the system 50 of FIG. 4, can detect and count the number of "on" compartments (but not the number of targets per compartment).

For each assay, the bulk concentration needs to be calculated using a certain inference method. The digital-variable-volume (DVV) and digital-variable-volume-approximation (DVVA) methods are based on maximum likelihood estimation; the concentration estimate is the one that maximizes the likelihood of observing a certain experimental result. The choice of maximum likelihood estimation was inspired by its use in multivolume digital PCR (where each assay utilizes a handful of predetermined, precisely controlled volumes), which has been inspired by limiting dilution assays for microorganism counting. In particular, an important feature is that results from different volumes are readily combined by way of multiplying the likelihoods. Below, are derived the expressions used to calculate the concentration estimates and the standard errors using the maximum likelihood framework. The terms relevant to the descriptions of the DVV and DVVA methods are described in Table 1.

TABLE 1

Definitions of mathematical symbols.

| Symbol | Definition |
|---|---|
| $\hat{x}$ | Estimator of a particular parameter denoted as x |
| $\langle x \rangle$ | Expectation of the quantity x over a certain distribution |
| $\lambda_T$ | Bulk concentration (number of targets/unit volume) |
| $\hat{\lambda}_T$ | Estimator of $\lambda_T$ (inferred from the assay result) |
| $\Lambda \equiv \ln(\lambda_T)$ | Natural log of bulk concentration |
| $\hat{\Lambda}$ | Estimator of $\Lambda$ (inferred from the assay result) |
| $\sigma_{\hat{\Lambda}}$ | Standard error of $\hat{\Lambda}$ |
| $\Lambda_0$ | $\hat{\Lambda}$ with smallest $\sigma_{\hat{\Lambda}}$ |
| N | Total number of compartments |
| $V_{total}$ | Total volume of compartments |
| A | Number of ON compartments |
| $A \equiv \{v_1, v_2, \ldots v_a\}$ | Set of volumes of ON compartments |
| b ≡ n − a | Number of OFF compartments |
| $V_b \overset{def}{=} \sum_{i=1}^{b} v_i$ | Total Volume of OFF compartments |

TABLE 1-continued

Definitions of mathematical symbols.

| Symbol | Definition |
|---|---|
| M | Number of pre-measured (test or characterization) volumes |
| $M \equiv \{v_1, v_2, \ldots v_m\}$ | Set of pre-measured (test or characterization) volumes |
| f(v) | Volume probability density function |
| $\mu_v$ | Mean volume |
| $\sigma_v$ | Standard deviation of volume |
| $\mu_{ln}V$ | Geometric mean of volume |
| W | Product logarithm function (also known as Lambert W function) |

Begin by calculating the probability that a particular compartment turns "on" given the volume and bulk concentration (equation (a)). It is the same as the probability of having more than one target in the compartment, based on the Poisson distribution with the mean of $v\lambda_T$. This probability is useful in subsequent derivation steps.

$$p_{each}(\lambda_T, v) = 1 - Prob(no\,targets) = 1 - \left.\frac{(v\lambda_T)^k e^{-v\lambda_T}}{k!}\right|_{k=0} = 1 - e^{-v\lambda_T} \quad (a)$$

Digital Variable Volume (DVV)

The likelihood $l(\lambda_T)$ of observing a certain assay result, i.e., particular numbers of "on" and "off" compartments (a and b, respectively) with the associated volumes is the product of individual likelihoods calculated using equation (a).

$$\Pi_{i=1}^{a} p_{each}(\lambda_T, v_i) \Pi_{i=1}^{b} [1 - p_{each}(\lambda_T, v_i)] = \Pi_{i=1}^{a}(1 - e^{-v_i\lambda_T}) \Pi_{1}^{b} e^{-v_i\lambda_T} \quad (b)$$

The value of $\lambda_T$ that maximizes $l(\lambda_T)$ is then found. Use the natural logarithm of the concentration ($\Lambda \equiv \ln(\lambda_T)$) and the loglikelihood function ($L(\Lambda) \equiv \ln(\lambda_T)$) to conveniently calculate the standard errors and enforce the requirement for positive concentrations. The calculation of the standard error is also more appropriate for $\Lambda$ than for $\lambda_T$ because the distribution of $\hat{\Lambda}$ is less skewed. Therefore, the goal is now finding the $\Lambda$ value that maximizes $L(\Lambda)$. The expression for $L(\Lambda)$ and the first and second derivatives are shown below.

$$L(\Lambda) = \sum_{i=1}^{a} \ln\left(1 - e^{-v_i e^{\Lambda}}\right) - e^{\Lambda} \sum_{i=1}^{b} v_i \quad (c)$$

$$= \sum_{i=1}^{a} \ln\left(1 - e^{-v_i e^{\Lambda}}\right) - e^{\Lambda}\left(V_{total} - \sum_{i=1}^{a} v_i\right)$$

$$= \sum_{i=1}^{a} \left[\ln\left(1 - e^{-v_i e^{\Lambda}}\right) + v_i e^{\Lambda}\right] - V_{total} e^{\Lambda}$$

$$L'(\Lambda) = e^{\Lambda}\left(\sum_{i=1}^{a} \frac{v_i}{1 - e^{-v_i e^{\Lambda}}} - V_{total}\right) \quad (d)$$

$$L''(\Lambda) = e^{\Lambda}\left(\sum_{i=1}^{a} \frac{v_i}{1 - e^{-v_i e^{\Lambda}}} - V_{total}\right) - e^{2\Lambda}\sum_{i=1}^{a} \frac{v_i^2 e^{-v_i e^{\Lambda}}}{\left(1 - e^{-v_i e^{\Lambda}}\right)^2} \quad (e)$$

To calculate $\hat{\Lambda}$, the root of the first derivative (equation (d)) is determined, i.e., equation (1), which is repeated below, is solved.

$$\sum_{i=1}^{a} \frac{v_i}{1 - e^{-v_i \lambda_T}} = V_{Total} \quad (1)$$

Plugging $L'(\Lambda)=0$ into equation (e) gives $L''(\Lambda)<0$. So the $\Lambda$ value found using equation (1) indeed maximizes $L(\Lambda)$. Also, using the derivatives at $\Lambda$, the standard error of $\Lambda$ also can be calculated using the observed Fisher information $L''(\hat{\Lambda})$.

$$\sigma_{\hat{\Lambda}} = \sqrt{\text{variance}} = \sqrt{\frac{1}{-L''(\hat{\Lambda})}} = 1 / \sqrt{e^{2\hat{\Lambda}} \cdot \sum_{i=1}^{a} \frac{v_i^2 e^{-v_i \hat{\Lambda}}}{(1 - e^{-v_i \hat{\Lambda}})^2}} \quad (f)$$

This $\sigma_{\hat{\Lambda}}$ can be used to calculate the confidence interval. Calculating $\sigma_{\hat{\Lambda}}$ using the expected Fisher information is not feasible because the volume distribution is unknown. In fact, to implement the DVV technique, the volume distribution is not required and need not be the same from one experiment to another.

Digital Variable Volume Approximation (DVVA)

In general, the probability a compartment turns ON can be calculated using the volume distribution (specified by the probability density function $f(v)$).

$$p_{on}(\lambda_T) = \int f(v) p_{each}(\lambda_T, v) dv = \int f(v)(1 - e^{-v\lambda_T}) dv = 1 - \int f(v) e^{-v\lambda_T} dv \quad (g)$$

Previously, $f(v)$ has been chosen to follow the gamma distribution or truncated normal distribution. However, in practice, $f(v)$ may not be described by a simple function. And even when that is true, a set of pre-measured volumes (M as in Table 1) still needs to be experimentally obtained to characterize $f(v)$. Therefore, for the DVVA technique, a set of separately measured volumes, M, is used instead of $f(v)$.

$$p_{on}(\lambda) = 1 - \sum_{i=1}^{m} \frac{1}{m}(e^{-v_i \lambda_T}) = 1 - \frac{1}{m}\left(\sum_{i=1}^{m} e^{-v_i \lambda_T}\right) \quad (h)$$

The likelihood function can then be obtained using the binomial distribution (for the case of a ON compartments out of n compartments with the probability of $p_{on}(\lambda)$.

$$l(\lambda_T) = \binom{n}{a} p_{ON}^a (1 - p_{ON})^{n-a} = \binom{n}{a} \left[1 - \frac{1}{m}\left(\sum_{i=1}^{m} e^{-v_i \lambda_T}\right)\right]^a \left[\frac{1}{m}\left(\sum_{i=1}^{m} e^{-v_i \lambda_T}\right)\right]^{n-a} \quad (i)$$

As motivated above, the loglikelihood function can be calculated with the change of variable $\Lambda \equiv \ln(\lambda_T)$, and subsequently, its first and second derivatives.

$$L(\Lambda) = (a)\ln\left(1 - \frac{\sum_{i=1}^{m} e^{-v_i e^\Lambda}}{m}\right) + (n-a)\ln\left(\frac{\sum_{i=1}^{m} e^{-v_i e^\Lambda}}{m}\right) + \ln\binom{n}{a} \quad (j)$$

$$L'(\Lambda) = \frac{\left(\frac{a}{n} - 1 + \frac{1}{m}\sum_{i=1}^{m} e^{-v_i e^\Lambda}\right)\frac{n}{m}\sum_{i=1}^{m} v_i e^{\Lambda - v_i e^\Lambda}}{\left(1 - \frac{1}{m}\sum_{i=1}^{m} e^{-v_i e^\Lambda}\right)\frac{1}{m}\sum_{i=1}^{m} e^{-v_i e^\Lambda}} = \frac{\left[\frac{a}{n} - p_{ON}(e^\Lambda)\right]\frac{n}{m}\sum_{i=1}^{m} v_i e^{\Lambda - v_i e^\Lambda}}{p_{ON}(e^\Lambda)[1 - p_{ON}(e^\Lambda)]} \quad (k)$$

$$L'' = L'(\Lambda)e^\Lambda \left[1 - \frac{\frac{1}{m}\sum_{i=1}^{m} v_i e^{-v_i e^\Lambda}}{p_{ON}(e^\Lambda)} - \frac{\sum_{i=1}^{m} v_i^2}{\sum_{i=1}^{m} v_i e^{v_i}}\right] - \frac{ne^{2\Lambda}\left(\frac{1}{m}\sum_{i=1}^{m} v_i e^{-v_i e^\Lambda}\right)^2}{[1 - p_{ON}(e^\Lambda)]} \quad (l)$$

To maximize $L(\Lambda)$, the root of $L'(\Lambda)$ is found (equation (2), which is repeated below), and it is verified that it corresponds to a maximum by checking the sign of the second derivative (equation (m)). An interesting observation is that equation (2) can be obtained by using $a/n$ to estimate $p_{ON}(\lambda_T)$ $$0 = L'(\Lambda) = \frac{a}{n} - 1 + \frac{1}{m}\left(\sum_{i=1}^{m} e^{-v_i \lambda_T}\right) = \frac{a}{n} - p_{ON}(e^\Lambda) = \frac{a}{n} - p_{ON}(\lambda_T) \quad (2)$$

$$L''(\Lambda)|_{\Lambda=\hat{\Lambda}} = L''(\Lambda)|_{L'(\Lambda)=0} = 0 - \frac{ne^{2\Lambda}\left(\frac{1}{m}\sum_{i=1}^{m} v_i e^{-v_i e^\Lambda}\right)^2}{p_{ON}(e^\Lambda)} < 0 \quad (m)$$

Then $\sigma_{\hat{\Lambda}}$ is calculated using the expected Fisher information, $-\langle L''(\Lambda)\rangle$. The second derivative, $L''(\Lambda)$, is a linear function of $$\frac{a}{n} - p_{ON}(e^\Lambda)\left\{\frac{a}{n} - p_{ON}(e^\Lambda)\right\} = 0. \quad ((\text{equation 2}))$$

can be plugged into equation (k), and the subsequent result can be plugged into equation (l) to obtain the following expression for $\sigma_{\hat{\Lambda}}$.

$$\sigma_{\hat{\Lambda}} = \sqrt{\text{variance}} = \sqrt{\frac{1}{-\langle L''(\Lambda)\rangle}} = \frac{1}{(e^\Lambda)} \sqrt{\frac{p_{on}(e^\Lambda) \cdot \left[1 - p_{on}(e^\Lambda)\right]}{n\left(\frac{1}{m}\sum_{i=1}^{m} v_i e^{-v_i e^\Lambda}\right)}} \quad (n)$$

In this particular case, the standard error calculated using the observed Fisher information, $-L''(\Lambda)$, is also the same as equation (n) evaluated at $\Lambda=\hat{\Lambda}$. This can be verified by plugging $L'(\hat{\Lambda})=0$ into $L''(\vec{\Lambda})$ (equation (l)).

EXAMPLE EMBODIMENTS

Example 1 includes a system, comprising: a device configured to generate compartments of a sample, at least one of the compartments having a respective volume that is different from a respective volume of each of at least another one of the compartments; a detector configured to determine a number of the compartments each having a respective number of a target that is greater than a threshold number of the target; and electronic circuitry configured to determine a bulk concentration of the target in a source of the sample in response to the determined number of the compartments.

Example 2 includes the system of Example 1 wherein the device includes a container configured to generate the compartments of the sample in a barrier phase in response to the container moving.

Example 3 includes the system of any of Examples 1-2 wherein the device includes a container configured to generate the compartments of the sample in a liquid in response to a shaking of the container.

Example 4 includes the system of any of Examples 1-3 wherein the device includes a container configured to generate the compartments of the sample as droplets of the sample in an oil in response to a shaking of the container.

Example 5 includes the system of any of Examples 1-4 wherein the device includes a container configured to generate the compartments of the sample as droplets of the sample in a barrier phase in response to a shaking of the container, the droplets each have a viscosity, the barrier phase having a viscosity that is greater than the viscosity of the droplets.

Example 6 includes the system of any of Examples 1-5 wherein the detector is configured to determine the number of the compartments each having a respective number of the target that is greater than the threshold number of the target in response to a wavelength of electromagnetic energy at which each of the number of the compartments luminesces.

Example 7 includes the system of any of Examples 1-6 wherein the detector is configured to determine the number of the compartments each having a respective number of the target that is greater than the threshold number of the target in response to a wavelength of electromagnetic energy that each of the number of the compartments absorbs.

Example 8 includes the system of any of Examples 1-7 wherein the detector is configured to determine the number of the compartments each having a respective number of the target that is greater than the threshold number of the target in response to a wavelength of electromagnetic energy that each of the number of the compartments passes.

Example 9 includes the system of any of Examples 1-8 wherein the detector is configured to determine the number of the compartments each having a respective number of the target that is greater than the threshold number of the target in response to a wavelength of electromagnetic energy that each of the number of the compartments blocks.

Example 10 includes the system of any of Examples 1-9 wherein the electronic circuitry is configured to determine a bulk concentration of the target in a source of the sample in response to a respective measured volume of each of the number of compartments.

Example 11 includes the system of any of Examples 1-10 wherein the electronic circuitry is configured to determine a bulk concentration of the target in a source of the sample in response to a sum of a respective measured volume of each of the compartments.

Example 12 includes the system of any of Examples 1-11 wherein the electronic circuitry is configured to determine a bulk concentration of the target in a source of the sample in response to a number of the compartments.

Example 13 includes the system of any of Examples 1-12 wherein the electronic circuitry is configured to determine a bulk concentration of the target in a source of the sample in response to a number of other compartments.

Example 14 includes the system of any of Examples 1-13 wherein the electronic circuitry is configured to determine a bulk concentration of the target in a source of the sample in response to a respective measured volume of each of other compartments.

Example 15 includes the system of any of Examples 1-14 wherein the electronic circuitry is configured to determine a bulk concentration of the target in a source of the sample in response to a number of other compartments and a respective measured volume of each of the other compartments.

Example 16 includes the system of any of Examples 1-15 wherein the electronic circuitry is configured to determine a bulk concentration of the target in a source of the sample in response to a probability density function of compartment volume.

Example 17 includes a system, comprising: a barrier-phase liquid; a container configured to receive the barrier-phase liquid, to receive a sample including a target, and to generate compartments of the sample suspended in the barrier-phase liquid in response to a shaking of the container, at least one of the compartments having a respective volume that is different from a respective volume of each of at least another one of the compartments; and a detector configured to determine a number of the compartments each having a respective number of the target that is greater than a threshold number of the target.

Example 18 includes the system of Example 17 wherein the barrier-phase liquid includes an oil.

Example 19 includes the system of any of Examples 17-18 wherein the container includes a clear tube.

Example 20 includes the system of any of Examples 17-19 wherein the detector includes an electronic detector.

Example 21 includes the system of any of Examples 17-20 wherein the detector is configured to determine a number of the compartments.

Example 22 includes the system of any of Examples 17-21, further comprising an apparatus configured to obtain the sample from a source including the target.

Example 23 includes the system of any of Examples 17-22, further comprising a computer-readable medium storing instructions that, when executed by a computing circuit, cause the computing circuit to determine a bulk concentration of the target in a source of the sample in response to the number of the compartments each having a respective number of the target that is greater than a threshold number of the target.

Example 24 includes a method, comprising: generating compartments of a sample, at least one of the compartments having a respective volume that is different from a respective volume of each of at least another one of the compartments; determining a number of the compartments each having a respective number of a target that is greater than a threshold number of the target; and determining a bulk concentration of the target in a source of the sample in response to the number of the compartments.

Example 25 includes the method of Example 24 wherein generating the compartments includes generating the compartments suspended in a barrier phase by shaking a container that includes the sample and the barrier phase.

Example 26 includes the method of any of Examples 24-25 wherein generating the compartments includes generating droplets suspended in a liquid by shaking a container that includes the sample and the liquid.

Example 27 includes the method of any of Examples 24-26 wherein determining the number of compartments each having a respective number of the target that is greater than the threshold number of the target includes determining the number of compartments in response to a wavelength of electromagnetic energy at which each of the number of the compartments luminesces.

Example 28 includes the method of any of Examples 24-27 wherein determining the number of the compartments each having a respective number of the target that is greater than the threshold number of the target includes determining the number of compartments in response to a wavelength of electromagnetic energy that each of the number of the compartments absorbs.

Example 29 includes the method of any of Examples 24-28 wherein determining the number of the compartments each having a respective number of the target that is greater than the threshold number of the target includes determining the number of compartments in response to a wavelength of electromagnetic energy that each of the number of the compartments passes.

Example 30 includes the method of any of Examples 24-29 wherein determining the number of the compartments each having a respective number of the target that is greater than the threshold number of the target includes determining the number of compartments in response to a wavelength of electromagnetic energy that each of the number of the compartments blocks.

Example 31 includes the method of any of Examples 24-30 wherein determining the bulk concentration of the target in the source of the sample includes determining the bulk concentration in response to a respective measured volume of each of the number of compartments.

Example 32 includes the method of any of Examples 24-31 wherein determining the bulk concentration of the target in the source of the sample includes determining the bulk concentration in response to a sum of a respective measured volume of each of the compartments.

Example 33 includes the method of any of Examples 24-32 wherein determining the bulk concentration of the target in the source of the sample includes determining the bulk concentration in response to a number of the compartments.

Example 34 includes the method of any of Examples 24-33 wherein determining the bulk concentration of the target in the source of the sample includes determining the bulk concentration in response to a number of other compartments.

Example 35 includes the method of any of Examples 24-34 wherein determining the bulk concentration of the target in the source of the sample includes determining the bulk concentration in response to a respective measured volume of each of other compartments.

Example 36 includes the method of any of Examples 24-35 wherein determining the bulk concentration of the target in the source of the sample includes determining the bulk concentration in response to a number of other compartments and a respective measured volume of each of the other compartments.

Example 37 includes the method of any of Examples 24-36 wherein determining the bulk concentration of the target in the source of the sample includes determining the bulk concentration in response to a probability density function of compartment volume.

Example 38 includes a tangible non-transitory computer-readable medium storing instructions that, when executed by a computing circuit, cause the computing circuit: to determine a number of compartments of a sample each having a respective number of a target that is greater than a threshold number of the target, at least one of the compartments having a respective volume that is different from a respective volume of each of at least another one of the compartments; and to determine a bulk concentration of the target in a source of the sample in response to the determined number of compartments.

From the foregoing it will be appreciated that, although specific embodiments have been described herein for purposes of illustration, various modifications may be made without deviating from the spirit and scope of the disclosure. Furthermore, where an alternative is disclosed for a particular embodiment, this alternative may also apply to other embodiments even if not specifically stated. In addition, any described component or operation may be implemented/performed in hardware, software, firmware, or a combination of any two or more of hardware, software, and firmware. For example, any of one, more, or all of the above-described operations and functions can be performed by electronic circuitry that is hardwire configured to perform one or more operations or functions, that is configured to execute program instructions to perform one or more operations or functions, that is configured with firmware, or otherwise configured, to perform one or more operations or functions, or that is configured with a combination of two or more of the aforementioned configurations. For example, one or more of the components of the computer 54 of FIG. 11 can include such electronic circuitry. Furthermore, one or more components of a described apparatus or system may have been omitted from the description for clarity or another reason. Moreover, one or more components of a described apparatus or system that have been included in the description may be omitted from the apparatus or system. In addition, one or more steps of a described method may have been omitted from the description for clarity or another reason. Moreover, one or more steps of a described methods that have been included in the description may be omitted from the method.

The invention claimed is:

1. A method executed by a computing circuit, comprising:
generating compartments of a sample, at least one of the compartments having a respective volume that is different from a respective volume of each of at least another one of the compartments;
determining a characterized number of the compartments each having a respective number of a target that is greater than a threshold number of the target and a characterized volume for each of the compartments having the target greater than the threshold number; and
determining a bulk concentration of the target in a source of the sample by generating an estimate of the bulk concentration in response to the characterized number of the compartments having the target greater than the threshold number and the characterized volume for each of the compartments having the target greater than the threshold number, wherein the bulk concentration is determined by a digital-variable-volume-approximation (DVVA) algorithm.

2. The method of claim 1 wherein generating the compartments includes generating the compartments suspended in a barrier phase by shaking a container that includes the sample and the barrier phase.

3. The method of claim 1 wherein generating the compartments includes generating droplets suspended in a liquid by shaking a container that includes the sample and the liquid.

4. The method of claim 1 wherein determining the characterized number of compartments each having a respective number of the target that is greater than the threshold number of the target includes determining the characterized number of compartments in response to a wavelength of electromagnetic energy at which each of the number of the compartments luminesces.

5. The method of claim 1 wherein determining the characterized number of the compartments each having a respective number of the target that is greater than the threshold number of the target includes determining the characterized number of compartments in response to a wavelength of electromagnetic energy that each of the number of the compartments absorbs.

6. The method of claim 1 wherein determining the characterized number of the compartments each having a respective number of the target that is greater than the threshold number of the target includes determining the characterized number of compartments in response to a wavelength of electromagnetic energy that each of the number of the compartments passes.

7. The method of claim 1 wherein determining the characterized number of the compartments each having a respective number of the target that is greater than the threshold number of the target includes determining the characterized number of compartments in response to a wavelength of electromagnetic energy that each of the number of the compartments blocks.

8. The method of claim 1 wherein determining the bulk concentration of the target in the source of the sample includes determining the bulk concentration in response to a respective measured volume of each of the number of compartments.

9. The method of claim 1 wherein determining the bulk concentration of the target in the source of the sample includes determining the bulk concentration in response to a sum of a respective measured volume of each of the compartments.

10. The method of claim 1 wherein determining the bulk concentration of the target in the source of the sample includes determining the bulk concentration in response to a number of the compartments.

11. The method of claim 1 wherein determining the bulk concentration of the target in the source of the sample includes determining the bulk concentration in response to a number of other compartments.

12. The method of claim 1 wherein determining the bulk concentration of the target in the source of the sample includes determining the bulk concentration in response to a respective measured volume of each of other compartments.

13. The method of claim 1 wherein determining the bulk concentration of the target in the source of the sample includes determining the bulk concentration in response to a number of other compartments and a respective measured volume of each of the other compartments.

14. The method of claim 1 wherein determining the bulk concentration of the target in the source of the sample includes determining the bulk concentration in response to a probability density function of compartment volume.

15. The method of claim 1 wherein determining the bulk concentration of the target in the source of the sample includes determining a bulk concentration in response to a probability density function of compartment volume.

* * * * *